(12) United States Patent
Sheppard, Jr. et al.

(10) Patent No.: US 6,773,429 B2
(45) Date of Patent: Aug. 10, 2004

(54) MICROCHIP RESERVOIR DEVICES AND FACILITATED CORROSION OF ELECTRODES

(75) Inventors: Norman F. Sheppard, Jr., Bedford, MA (US); Christina M. Feakes, Brighton, MA (US); John T. Santini, Jr., Belmont, MA (US)

(73) Assignee: MicroCHIPS, Inc., Bedford, MA (US)

( * ) Notice: Subject to any disclaimer, the term of this patent is extended or adjusted under 35 U.S.C. 154(b) by 151 days.

(21) Appl. No.: 09/975,786

(22) Filed: Oct. 11, 2001

(65) Prior Publication Data

US 2002/0138067 A1 Sep. 26, 2002

Related U.S. Application Data

(60) Provisional application No. 60/239,373, filed on Oct. 11, 2000.

(51) Int. Cl.$^7$ .......................... A61K 9/22; A61M 31/00; A61B 5/05
(52) U.S. Cl. ...................... 604/891.1; 604/66; 600/345; 600/365
(58) Field of Search .................... 604/890.1, 891.1, 604/892.1, 65, 131; 600/309, 345, 347, 348, 365

(56) References Cited

U.S. PATENT DOCUMENTS

| | | |
|---|---|---|
| 3,560,358 A | 2/1971 | Black et al. |
| 3,798,141 A | 3/1974 | Yahalom et al. |
| 4,345,981 A | 8/1982 | Bennett et al. |
| 4,360,019 A | 11/1982 | Portner et al. |
| 4,585,652 A | 4/1986 | Miller et al. |
| 4,731,049 A | 3/1988 | Parsi |
| 4,793,825 A | 12/1988 | Benjamin et al. |
| 5,042,975 A | 8/1991 | Chien et al. |
| 5,167,625 A | 12/1992 | Jacobsen et al. |
| 5,200,051 A | 4/1993 | Cozzette et al. |
| 5,202,018 A | 4/1993 | Horányi et al. |
| 5,252,294 A | 10/1993 | Kroy et al. |
| 5,279,607 A | 1/1994 | Schentag et al. |
| 5,324,316 A | 6/1994 | Schulman et al. |

(List continued on next page.)

FOREIGN PATENT DOCUMENTS

| | | |
|---|---|---|
| DE | 197 16 683 | 6/1998 |
| WO | 93/03790 | 3/1993 |
| WO | 01/28629 | 4/2001 |
| WO | 01/37926 | 5/2001 |

OTHER PUBLICATIONS

Barilla et al., Optical Materials, 17(1–2):91–94 (2001).
Kwon, et al., "Electrically Erodible Polymer Gel for Controlled Release of Drugs," *Nature* 354:291–293 (1991).
Low, et al., "Microactuators Towards Microvalves for Responsive Controlled Drug Delivery," *Senors & Actuators B* 67: 149–60 (2000).

(List continued on next page.)

*Primary Examiner*—Manuel Mendez
*Assistant Examiner*—Mark K Han
(74) *Attorney, Agent, or Firm*—Sutherland Asbill & Brennan, LLP

(57) ABSTRACT

Methods and devices are provided for enhancing corrosion of an electrode in a biocompatible fluid. The method comprises (1) placing a primary electrode and a counter electrode in an electroconductive biocompatible fluid to form an electrochemical cell; and (2) applying a time-varying potential, through the electrochemical cell, to the primary electrode. In a preferred embodiment, the primary electrode is metal and comprises a reservoir cap of a microchip device for the release of molecules or exposure of device reservoir contents. The potential preferably is characterized by a waveform having a maximum potential effectively anodic to meet or exceed the corrosion potential of the primary electrode. Also, the minimum potential preferably is effectively cathodic to be below the value where re-deposition of metal ions on the metal electrode can substantially occur, thereby corroding the metal electrode.

40 Claims, 2 Drawing Sheets-

U.S. PATENT DOCUMENTS

| | | | |
|---|---|---|---|
| 5,336,213 | A | 8/1994 | D'Angelo et al. |
| 5,366,454 | A | 11/1994 | Currie et al. |
| 5,368,704 | A | 11/1994 | Madou et al. |
| 5,585,069 | A | 12/1996 | Zanzucchi et al. |
| 5,713,954 | A | 2/1998 | Rosenberg et al. |
| 5,797,898 | A | 8/1998 | Santini, Jr. et al. |
| 5,807,397 | A | 9/1998 | Barreras |
| 5,842,787 | A | 12/1998 | Kopf-Sill et al. |
| 5,962,081 | A | 10/1999 | Öhman et al. |
| 6,047,214 | A | 4/2000 | Mueller et al. |
| 6,114,658 | A | 9/2000 | Roth et al. |
| 6,123,861 | A | 9/2000 | Santini, Jr. et al. |
| 6,140,740 | A | 10/2000 | Porat et al. |
| 6,171,850 | B1 | 1/2001 | Nagle et al. |
| 6,243,608 | B1 | 6/2001 | Pauly et al. |

OTHER PUBLICATIONS

Madou & Florkey, "From Batch to Continuous Manufacturing of Microbiomedical Devices," *Chem. Rev.*, 100: 2679–92 (2000).

Madou, Fundamentals of Microfabrication, pp. 468–512 (CRC Press 1997).

Madou & He, "Exploitation of a Novel Artificial for Controlled Drug Delivery," pp. 495–497 (1999).

Surbled, et al., "Characterization of Sputtered TiNi Shape Memory Alloy Thin Films," *Jpn. J. Appl. Phys.* 38: L1547–L1549 (1999).

Surbled, et al., "Shape Memory Alloys for Micromembranes Actuation," *SPIE*. 3825: 63–70 (1999).

U.S. patent application Ser. No. 09/638,109, Santini, Jr. et al., filed Aug. 11, 2000.

U.S. patent application Ser. No. 09/715,493, Santini, Jr. et al., filed Nov. 17, 2000.

U.S. patent application Ser. No. 09/727,858, Richards et al., filed Dec. 01, 2000.

U.S. patent application Ser. No. 09/798,562, Santini, Jr. et al., filed Mar. 02, 2001.

U.S. patent application Ser. No. 09/975,786, Sheppard, Jr. et al., filed Oct. 11, 2001.

U.S. patent application Ser. No. 10/042,996, Santini, Jr. et al., filed Jan. 09, 2002.

Surbled, et al., "Array of Shape Memory Alloy One–Shot Mciro–Valves for Drug Delivery," MME '99, Gif sur Yvette, France (Sep. 27–28, 1999).

Tierney, et al., "New Electrorelease Systems Based on Microporous Membranes," *J. Electrochem. Soc.*, 137:3789–3793 (1990).

Tierney, et al., "Electroreleasing Composite Membranes for Delivery of Insulin and Other Biomacromolecules," *J. Electrochem. Soc.*, 137:2005–2006 (1990).

Frankenthal & Eaton, *J. Electrochem.* Soc., 123(5): 703–06 (1976).

Palmore & Whitesides, "Microbial and Enzymatic Biofuel Cells," *Enzymatic Conversion of Biomass for Fuel Production*, ACS Symposium Series 566:271–90 (1994).

Kano & Ikeda, "Fundamentals and practices of mediated bioelectrocatalysis," *Analytical Sci.*, 16(10):1013–21 (2000).

Wilkinson, Autonomous Robots, 9(2): 99–111 (2000).

Vladimirsky, et al., "Thin Metal Film Thermal Micro–Sensors," *Proc. SPIE–Int. Soc. Opt. Eng.* 2640:184–92 (1995).

Izumi, *J. Electroanal. Chem.*, 301:151–60 (1991).

Liu C., et al., "Applicaitons of microfabrication and micromachining techniques to biotechnology," *Trends in Biotechnology*, vol. 14, No. 6, pp 213–216.

Santini, Jr., et al. "Microchips as Controlled Drug Delivery Devices," *Angew. Chem. Int. Ed.*, vol. 39, pp. 2396–2407 (2000).

MICROCHIP RESERVOIR DEVICES AND FACILITATED CORROSION OF ELECTRODES

CROSS-REFERENCE TO RELATED APPLICATIONS

Priority is claimed under 35 U.S.C. § 119 to U.S. provisional application Ser. No. 60/239,373, filed Oct. 11, 2000.

BACKGROUND OF THE INVENTION

This invention relates to miniaturized devices for the controlled exposure or release of molecules such as drugs and/or secondary devices such as sensors.

Microchip devices for chemical and drug delivery and for controlled exposure of reservoir contents have been described in detail in U.S. Pat. No. 5,797,898; U.S. Pat. No. 6,123,861; PCT WO 01/64344; and PCT WO 01/35928. One group of embodiments of these microchip devices provides active release or exposure of the contents of a reservoir in the substrate of the device. "Active" is used to refer to those embodiments in which release or exposure is initiated at a particular time by the application of a stimulus to the device or a portion of the device. Typically, the stimulus is applied to a reservoir cap covering the filled reservoirs. In one embodiment, thin reservoir caps consist of thin metal films. These films can be prepared from metals, such as gold, copper, silver and other metals, using microelectronic fabrication methods, such as evaporation and sputtering. To expose the contents of the reservoir to the environment outside of the reservoir, the barrier properties of the reservoir cap can be compromised by the electrochemical dissolution of the metal film. This dissolution typically is accomplished by maintaining the electrical potential of the metal electrode sufficiently anodic to oxidize the film, thereby forming soluble metal cations. In this embodiment, the stimulus applied to initiate active release or exposure is application of an electrical potential to the reservoir cap.

An important application for these active microchip devices is to serve as an implantable device for the delivery of drugs. Due to its small size, the microchip device may be implanted in the body in a variety of locations, including, but not limited to, under the skin and in the peritoneal cavity. The reservoir caps therefore will be directly exposed to one or more various bodily fluids in vivo, which can affect the electrochemical corrosion of the reservoir caps. In many complex fluids, such as biological fluids, the presence of electroactive molecules, such as some proteins, in the fluid may result in other reactions at or in close proximity to the electrode (i.e. the thin metal film). These reactions may reduce the rate of dissolution of the electrode. Because the electrochemical dissolution of the metal film should be rapid and of an extent sufficient to compromise the integrity of the reservoir cap, it would be advantageous to facilitate or enhance the corrosion of the metal electrode, particularly when the electrode is exposed to a biological fluid.

The use of a time varying potential has been used to facilitate electrochemical etching of materials. For example, U.S. Pat. No. 5,202,018 discloses the use of alternating anodic and cathodic potentials to etch semiconductors for the purpose of determining the composition and electrical properties as a function of depth. The alternating potential acts to produce a uniform etching of the material.

The electrochemical dissolution of metal films is a widely used industrial process used for the manufacture of items such as microelectronics packaging and connectors. For example, Frankenthal & Eaton, *J. Electrochem. Soc.*, 123 (5): 703–06 (1976) describes the use of a time-varying potential in the etching of platinum thin films used in the manufacture of microelectronic circuits. The etching was conducted in a solution of hydrochloric acid. The authors refer to U.S. Pat. No. 3,560,358 and No. 3,798,141 that involved the etching of noble metals using alternating current in solutions containing chloride and cyanide. In these manufacturing processes, the electrochemical dissolution of the metal is carried out in an electrolyte of known composition, and which is generally chosen to optimize one or more aspects of the etching process such as rate or surface finish.

Electrochemical methods can be used to prevent or remediate the fouling of metal surfaces. For example, U.S. Pat. No. 4,345,981 discloses the use of alternating potentials to reduce biofouling in conductive aqueous systems. The basis of this method is applying a potential suitably anodic to oxidize water at the electrode surface. The resultant generation of oxygen gas and hydrogen ions prevents fouling of the metal surface. In another example, U.S. Pat. No. 4,627,900 discloses the use of alternating potentials to remove nickel sulfide scale in reactors. The buildup of sulfide scale in vessels used to extract metals from mineral ores is remediated by applying a periodic potential to the reactor vessel to electrochemically convert the scale to soluble products.

Potential cycling has also been used as a means for preparing metal electrodes for analytical use. For example, Izumi, *J. Electroanal. Chem.*, 301:151–60 (1991) discloses an electrochemical pretreatment to activate a gold electrode for electrochemical analysis. The pretreatment consists of cycling the electrode between −0.04 and 1.41 volts versus a saturated calomel electrode (SCE) in a solution of hydrochloric acid. After this treatment, the potential required for the oxidation of ascorbic acid at the electrode was reduced and the current increased. This improvement in the properties of the electrode was attributed to a structural rearrangement of the gold surface.

None of these references are directed to facilitating electrode corrosion, particularly in a biocompatible or biological fluid, especially when in vivo.

It is therefore an object of the present invention to provide methods and devices for facilitating or enhancing the corrosion of a metal electrode in a biocompatible fluid, particularly for electrodes implanted in vivo.

It is a further object of the present invention to provide methods and devices for facilitating or enhancing the corrosion of thin metal film reservoir caps of active microchip devices.

It is another object of the present invention to enhance active release or exposure of reservoir contents from microchip devices, particularly microchip devices exposed to a complex, biocompatible fluid.

These and other objects, features, and advantages of the present invention will become apparent upon review of the following detailed description of the invention taken in conjunction with the drawings and the appended claims.

SUMMARY OF THE INVENTION

Methods and devices are provided for enhancing corrosion of a primary electrode in a biocompatible fluid. In a preferred embodiment, the method comprises (1) placing a metal electrode and a counter electrode in contact with an electroconductive biocompatible fluid to form an electrochemical cell; and (2) applying a time-varying potential, through the electrochemical cell, to the metal electrode, wherein the potential is characterized by a waveform having a maximum potential effectively anodic to meet or exceed the corrosion potential of the metal electrode, thereby corroding the metal electrode. The waveform also may preferably have a minimum potential effectively cathodic to be below the value where re-deposition of metal ions on the metal electrode can substantially occur. In this way, if a metal oxide is formed at the anodic potential, which passivates the surface and prevents further corrosion, then by making the potential cathodic, this oxide can be reduced and thus removed to expose the metal surface again.

The primary electrode also can be or comprise a polymer.

The electrode preferably comprises a reservoir cap of a microchip device for the release of molecules or exposure of device reservoir contents. Preferred reservoir contents include drugs, sensors, and combinations thereof.

The electrochemical cell can consist of two electrodes or can further comprise a reference electrode, which is placed in contact with the biocompatible fluid.

The biocompatible fluid can be a biological fluid, such as blood, plasma, extracellular matrix, lymph, interstitial fluid, serum, saliva, urine, semen, cerebrospinal fluid, and gastrointestinal fluids. The fluid can be in vivo or in vitro. Examples of other biocompatible fluids include saline solutions, buffer solutions, pharmaceutical carrier solutions, and fermentation broths.

The waveform can be, for example, a square wave, sine wave, sawtooth wave, triangle wave, and combinations thereof. The potential can be applied at essentially any frequency; however, a frequency between about 1 and 10 Hz is preferred.

In another embodiment, a microchip device is provided for the release or exposure of reservoir contents in any electroconductive fluid. The device includes (1) a substrate having reservoirs containing contents, wherein the reservoirs have reservoir caps which comprise a metal electrode; and (2) a means for applying a time-varying potential to the metal electrode in an amount effective to corrode the metal electrode when placed in an electroconductive fluid, wherein the means comprises a counter electrode. Preferably, the time varying potential is characterized by a waveform having a maximum potential effectively anodic to meet or exceed the corrosion potential of the metal electrode. In some embodiments, the waveform preferably has a minimum potential effectively cathodic to be below the value where re-deposition of metal ions on the metal electrode can substantially occur. The metal electrode preferably comprises gold, platinum, or silver, and preferably has a thickness between about 100 and 1000 nm.

DETAILED DESCRIPTION OF THE INVENTION

It was discovered that the electrochemical dissolution of a thin metal film (i.e. a metal electrode) in a biological fluid could be facilitated by maintaining a time-varying anodic potential to the electrode. From this finding, methods have been developed for using alternating electrical potentials to facilitate the corrosion of metal electrodes in electroconductive biocompatible fluids.

The Electrochemical Cell and Time-Varying Potential Method

The method preferably comprises placing a metal electrode and a counter electrode in an electroconductive biocompatible fluid to form an electrochemical cell; and applying a time-varying potential, through the electrochemical cell, to the metal electrode. The electrochemical dissolution of the metal electrode is accomplished by maintaining the electrical potential of the metal electrode sufficiently anodic to oxidize (i.e. corrode) the metal electrode, forming soluble metal cations.

Time-Varying Electrical Potential

Preferably, the electrical potential is characterized by a waveform having a maximum potential effectively anodic to meet or exceed the corrosion potential of the metal electrode, and a minimum potential effectively cathodic to be below the value where re-deposition of metal ions on the metal electrode can substantially occur, thereby corroding the metal electrode.

Figure 3:
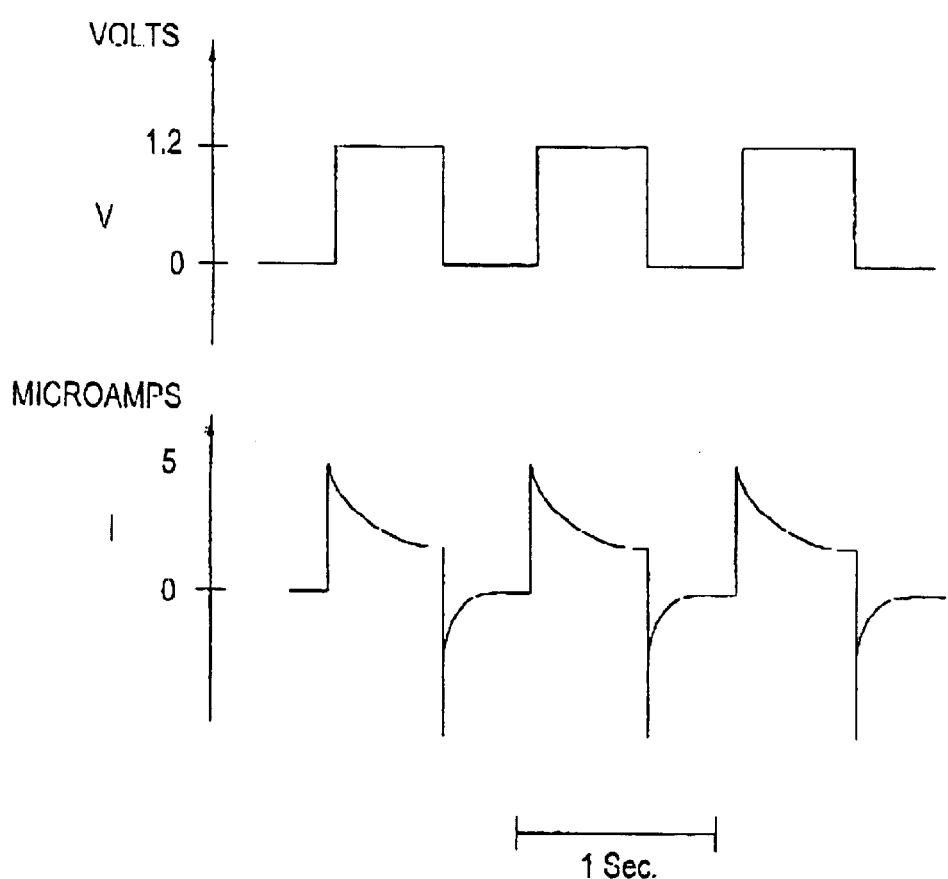
FIG. 3 illustrates typical voltage and current traces obtained during electrochemical dissolution of a gold microchip electrode.

The frequency of the waveform affects the corrosion rate of the metal film. The potential can be applied at a frequency between about 0.1 and 10,000 Hz, preferably between about 1 and 100, more preferably between about 1 and 10. The nature of the time-varying potential could be a square wave, sine wave, triangle wave (symmetric triangle), sawtooth wave (asymmetric triangle), or combinations thereof. A typical waveform is illustrated in FIG. 3.

Electrodes

The electrochemical cell consists of at least two electrodes: the primary electrode (i.e. the anode) and the counter electrode (i.e. the cathode). The electrochemical cell optionally can further comprise a reference electrode, which also is placed in contact with the biocompatible fluid. The primary electrode preferably comprises a metal or metal alloy. Alternatively, the primary electrode can comprise a polymer.

The metal electrode can be made from various metal materials. Selection of the appropriate material depends upon the particular application. Examples of such factors include the biocompatible fluid, whether corrosion is in vivo or in vitro, the size of the metal electrode, and the corrosion/dissolution rate desired. Suitable metal electrode materials include gold, platinum, silver, aluminum, chromium, copper, molybdenum, nickel, palladium, tantalum, titanium, tungsten, and zinc, as well as various metal alloys. Gold and platinum typically are preferred for in vivo applications.

In another embodiment, the electrode comprises a polymer, such as an electrical erodible (corrodible) polymer. See, e.g., I. C. Kwon and Y. H. Bae, "Electrically erodible polymer gel for controlled release of drugs", Nature, 354, 291–3 (1991). See also, Shiga, "Deformation and viscoelastic behavior of polymer gels in electric fields", NEUTRON SPIN ECHO SPECTROSCOPY VISCOELASTICITY RHEOLOGY, ADVANCES IN POLYMER SCIENCE 134:131–163 1997; Bae, et al., PULSATILE DRUG-RELEASE BY ELECTRIC STIMULUS, POLYMERIC DRUGS AND DRUG ADMINISTRATION, ACS SYMPOSIUM SERIES, 545: 98–110 1994; and Kwon, et al., CHARACTERISTICS OF CHARGED NETWORKS UNDER AN ELECTRIC STIMULUS, J. POLYMER SCIENCE PART B-POLYMER PHYSICS, 32 (6): 1085–1092 Apr. 30, 1994.

In a preferred embodiment, the metal electrode is in the form of a thin metal film having a thickness between about 10 and 10,000 nm, more preferably between about 100 and 1000 nm. In another preferred embodiment, the metal electrode forms at least a portion of a reservoir cap of a microchip device for the release of molecules or exposure of device reservoir contents. For example, the reservoir cap can be an anode, such that upon application of an electric potential between a cathode and the anode, the reservoir cap is oxidized to facilitate its disintegration, thereby exposing the reservoir contents to a surrounding fluid. It should be noted, however, that the dissolution which follows formation of soluble metal cations (upon oxidation) need not be complete in order to trigger release or exposure of reservoir contents, since release or exposure can occur upon mechanical failure (e.g., fracture) of the remaining structure of reservoir cap that is weakened from the incomplete oxidation/dissolution.

The counter electrode can be made of the same or different materials and sizes as the primary electrode. However, the counter electrode (cathode) for the microchip device embodiments would not typically be part of the reservoir cap; rather the counter electrode would be fabricated onto or adjacent to the anodic metal electrode.

As used herein, the term "counter electrode" refers generically to an auxiliary electrode in a three-electrode cell or to the counter electrode in a two-electrode cell, unless otherwise explicitly indicated.

In some embodiments, a pacemaker or defibrillator reference electrode may serve as the reference electrode in the methods and devices described herein.

Electroconductive Fluid

The electroconductive fluid into the electrodes are placed to form the electrochemical cell preferably is a biocompatible fluid. The biocompatible fluid can be a biological fluid. Representative biological fluids include blood, plasma, extracellular matrix, interstitial fluid, serum, saliva, semen, urine, cerebrospinal fluid, gastrointestinal fluids, and essentially any other fluid environment in which a microchip device or electrode may be implanted in the body of a human or animal. The biological fluid can be in vivo or ex vivo. The biocompatible fluid need not be biologically derived; for example, it could be a saline solution, a buffer solution, a sugar solution, irrigation fluids, or a fermentation broth. In one embodiment, the biocompatible fluid is a pharmaceutically acceptable carrier solution suitable for in vivo administration.

The electroconductive fluid also could be a water sample that is being tested. For example, the microchip device can test water for the presence or absence of various impurities and contaminants, such as the presence of a chemical or biological warfare agent.

Non-biocompatible electroconductive fluids also can be used with microchip device electrodes in ex vivo applications, such as for some diagnostic assays, sensors, and fragrance release, for example.

Microchip Device Embodiments

Figure 1:
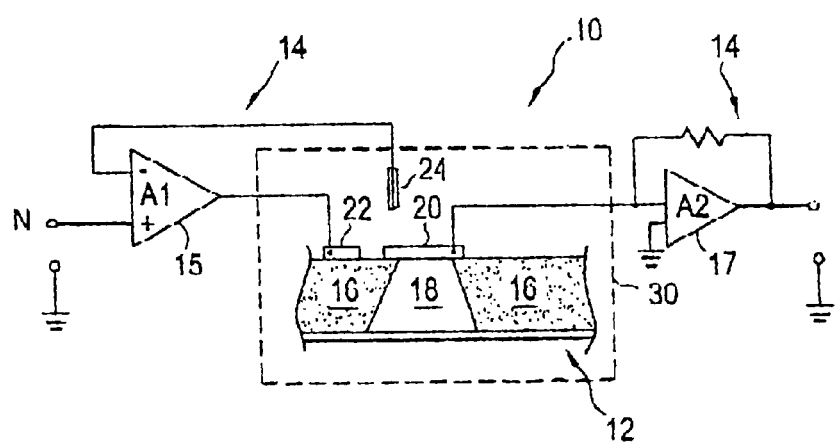
FIG. 1 is a schematic illustration of a three-electrode cell used for the electrochemical dissolution of a microchip reservoir cap.

FIG. 1 illustrates a device 10 comprising a three-electrode electrochemical cell and potentiostat circuit 14 used for the corrosion and dissolution of a microchip reservoir cap 20. The microchip device 12 includes a substrate 16 and a reservoir 18, which is sealed by a reservoir cap 20. The electrochemical cell includes the reservoir cap 20 (configured as the working electrode, i.e. the metal electrode), an auxiliary electrode 22, a reference electrode 24, and an electroconductive fluid 30. The potential of the metal electrode 20 may be maintained at a fixed value and the current passing through the electrode may be measured using amplifier 17. The auxiliary electrode 22 in this embodiment is fabricated on the substrate 16 of the microchip device 12. The auxiliary electrode 22 is driven by amplifier 15 to maintain the potential between the reference electrode 24 and the reservoir cap 20 equal to the control voltage. The reference electrode 24 may be in the form of a standard reference (e.g., a silver wire) or an electrode fabricated on the microchip device 12.

Figure 2:
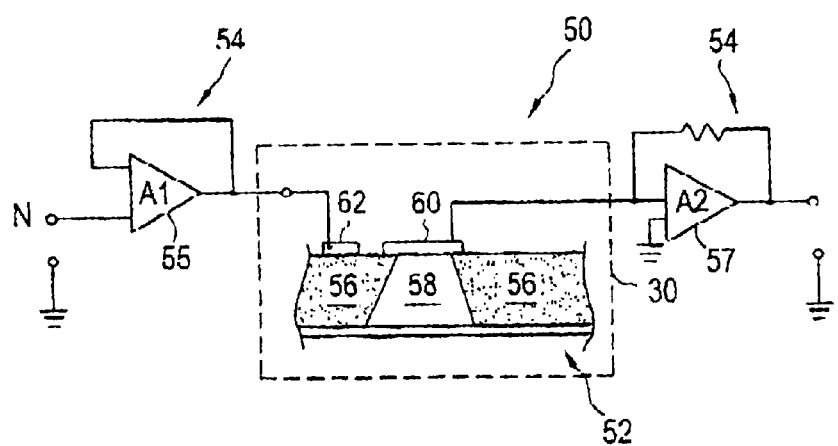
FIG. 2 is a schematic illustration of a two-electrode cell used for the electrochemical dissolution of a microchip reservoir cap.

FIG. 2 illustrates a device 50 comprising a two-electrode electrochemical cell and potentiostat circuit 54 used for the corrosion and dissolution of a microchip reservoir cap 60. The microchip device 52 includes a substrate 56 and a reservoir 58, which is sealed by reservoir cap 60. The electrochemical cell includes the reservoir cap 60 (configured as the working electrode, i.e. the metal electrode), a counter electrode 62, and an electroconductive fluid 30. The counter electrode 62 is driven by amplifier 55 to maintain the potential between the counter electrode 62 and the reservoir cap 60 equal to the control voltage. The potential of the metal electrode 60 may be maintained at a fixed value and the current passing through the electrode may be measured using amplifier 57. The counter electrode 62 in this embodiment is fabricated on the substrate 56 of the microchip device 52.

The potentiostat circuitry illustrated in FIGS. 1 and 2 represents only one possible design. Other suitable circuit configurations are known or can be readily created. For example, see Kissinger, "Introduction to Analog Instrumentation", Ch. 6, Laboratory Techniques in Electroanalytical Chemistry, P. T. Kissinger & W. R. Heineman, eds. (Marcel Dekker, New York 1996).

Other Features of the Microchip Device

Each microchip device includes a substrate having a plurality of reservoirs (as described, for example, in U.S. Pat. No. 5,797,898 to Santini, et al.), and contents contained in the reservoirs. The reservoir cap controls the time of release or exposure of the contents.

The microchip reservoir contents can be essentially any chemical or miniature device. In a preferred embodiment, the chemical is a therapeutic, prophylactic, or diagnostic agent. (The term "drug" is used herein to refer any of these agents.) Preferred drug delivery applications include potent compounds, including both small and large (i.e. macro) molecules, such as hormones, steroids, chemotherapy medications, vaccines, gene delivery vectors, and some strong analgesic agents. An example of a diagnostic agent is a contrast agent or radio-labeled material, which may be used for example in diagnostic imaging. Other molecules that can be released include fragrances and flavoring agents.

The reservoir contents also can be catalysts (e.g., zeolites, enzymes), one or more reagents, or a combination thereof. In another embodiment, the reservoir content includes a secondary device such as a sensor and sensing component, e.g., a biosensor. As used herein, the term "biosensor" includes, but is not limited to, sensing devices that transduce the chemical potential of an analyte of interest into an electrical signal, as well as electrodes that measure electrical signals directly or indirectly (e.g., by converting a mechanical or thermal energy into an electrical signal). For example, the biosensor may measure intrinsic electrical signals (EKG, EEG, or other neural signals), pressure, temperature, pH, or loads on tissue structures at various in vivo locations. The electrical signal from the biosensor can then be measured, for example by a microprocessor/controller, which then can transmit the information to a remote controller, another local controller, or both. Examples of sensing components include components utilized in measuring or analyzing the presence, absence, or change in a chemical or ionic species, electromagnetic or thermal energy (e.g., light), or one or more physical properties (e.g., pH, pressure) at a site. The contents may either be released from or remain immobilized in the reservoir, depending on the particular application. Individual reservoirs may contain multiple types of chemicals, multiple types of devices, or combinations of devices and chemicals.

Methods of Fabricating the Devices

The basic microchip devices (i.e. substrate, reservoirs, reservoir caps, and release system) can be made and assembled using microfabrication methods known in the art, particularly those methods described in U.S. Pat. No. 5,797,898 and No. 6,123,861, both to Santini, et al., and PCT WO 01/64344, WO 01/41736, WO 01/35928, and WO 01/12157, which are all herein incorporated by reference in their entirety.

The metal electrodes, counter electrodes, and auxiliary electrodes, as well as the associated wiring and electronic components preferably are made and assembled using standard microelectronic fabrication techniques known in the art. For example, techniques for forming thin metal film electrodes include sputtering, evaporation, and chemical vapor deposition.

Use of the Microchip Devices

The microchip device systems can be used in a wide variety of applications. The applications can be ex vivo or in vitro, but more preferably are for in vivo applications, particularly following non- or minimally-invasive implantation. The microchips can be implanted via surgical procedures or injection, or swallowed, and can deliver many different drugs, at varying rates and varying times.

Preferred applications for using the devices and systems include the controlled delivery of a drug (i.e. a therapeutic, prophylactic, or diagnostic agent) to sites within the body of a human or animal, biosensing, or a combination thereof. The microchip systems are especially useful for drug therapies in which it is desired to control the exact amount, rate, and/or time of delivery of the drug. Preferred drug delivery applications include the delivery of potent compounds, including both small and large molecules, such as hormones, steroids, chemotherapy medications, vaccines, gene delivery vectors, and some strong analgesic agents.

In another preferred embodiment, the microchip device includes one or more biosensors (which may be sealed in reservoirs until needed for use) that are capable of detecting and/or measuring signals within the body of a patient. For example, the system can be used to relay or record information on the patient's vital signs or the implant environment, such as blood gases, drug concentration, or temperature.

The system also has a variety uses that are not limited to implantation. For example, the reservoir contents may include a sensor for detecting a chemical or biological molecule at the site in which the microchip is placed, and a telemetry system transmits a status of the sensor detection to a remote receiver and/or controller. Such a site could be in vivo or in vitro.

The microchip devices have numerous other applications. The microchip devices can deliver precisely metered quantities of molecules and thus are useful for in vitro applications, such as analytical chemistry and medical diagnostics, as well as biological applications such as the delivery of factors to cell cultures.

As another example, the reservoir contents may include (1) a sensor for detecting at a site a chemical or biological molecule useful as an agent for chemical or biological warfare and/or (2) an antidote molecule for release once the weapon molecule is detected. Such a microchip device could be integrated into an early warning/detection system.

The invention can further be understood with reference to the following non-limiting examples.

EXAMPLE 1
In Vitro Corrosion of Gold Electrode

A 3 mm diameter solid gold electrode was polished to a mirror finish using polishing compounds. Then, the electrode was sonicated in methanol to remove any residual grit. The electrode subsequently was immersed in bovine calf serum, along with a silver/silver chloride reference electrode and a platinum auxiliary electrode. An electrochemical cell was formed with the gold electrode as the working electrode, the platinum electrode as the auxiliary electrode, and the silver/silver chloride as the reference electrode. A potentiostat was used to apply a time-varying potential in the form of 1 Hz square wave to the working electrode.

In different experiments, the potential of the more anodic phase of the waveform was varied between 1.05 and 1.35 volts with respect to the reference, and the potential of the more cathodic phase of the waveform varied between 0.25 and 0.65 volts with respect to the reference. Following a 10 minute application of the time-varying potential, the electrode was rinsed, dried, and examined under a microscope for evidence of corrosion, discoloration, and/or loss of the mirror finish. The results of these experiments are summarized in Table 1 below.

TABLE 1

Electrode Corrosion vs. Magnitude of Time-Varying Potential

| Vmin | 0.65 | 0.55 | 0.45 | 0.40 | 0.35 | 0.25 | 0.35 | 0.35 | 0.35 |
|---|---|---|---|---|---|---|---|---|---|
| Vmax | 1.35 | 1.35 | 1.35 | 1.35 | 1.35 | 1.35 | 1.25 | 1.15 | 1.05 |
| Corrodes? | No | No | No | No | Yes | Yes | Yes | Yes | No |

The results indicate that corrosion of the gold electrode occurred in serum when the potential of the anodic phase of the waveform was greater than or equal to 1.15 volts, and the potential of the cathodic phase of the waveform was less than 0.40 volts, all potentials being expressed relative to the silver/silver chloride reference electrode. This system worked where the maximum electrode potential was anodic to the corrosion potential and the minimum electrode potential was at or below the gold re-deposition potential.

EXAMPLE 2
In Vivo Corrosion of Gold Microchip Reservoir Caps

Microchip devices were prepared with 300 nm thick gold reservoir caps using processes similar to those described in U.S. Pat. No. 6,123,861 to Santini, Jr. et al. A gold cathode was also provided on the microchip substrate. The microchip was mounted on a printed circuit board. Gold wire, having a diameter of 0.0015" (38 $\mu$m), was used to connect the leads on the chip to the printed circuit board. Wires were soldered to the printed circuit board to make connections to the printed circuit board. A 0.25 mm diameter silver wire reference electrode was tacked to the printed circuit board chip carrier with epoxy.

The microchip assembly was implanted subcutaneously in the back of a female Sprague Dawley rat, and the leads were routed through the incision (used to form the implantation pocket). The electrochemical cell was composed of a first reservoir cap serving as the working electrode, the on-chip cathode serving as the auxiliary electrode, and the silver wire serving as the reference electrode.

A potentiostat was used to apply a 1 Hz square wave having an amplitude of 1.2 volts, centered on 0.6 volts, with respect to the silver wire reference. (This alternatively could be described as a waveform with a max of 1.2 volts, and a minimum of 0 volts.) The potential was applied to the first reservoir cap for a period of ten minutes.

The working electrode connection of the potentiostat was connected to a second reservoir cap. A DC potential of 1.15 volts with respect to the silver wire reference was applied to the second reservoir cap for a period of five minutes.

The microchip assembly then was explanted and examined under a microscope. The first reservoir cap, which had been cycled, was severely corroded, while the second reservoir cap, which had been maintained at a constant potential, showed no signs of corrosion.

Modifications and variations of the methods and devices described herein will be obvious to those skilled in the art from the foregoing detailed description. Such modifications and variations are intended to come within the scope of the appended claims.

We claim:

1. A method for enhancing corrosion of an electrode in a biocompatible fluid, the method comprising:
    placing a primary electrode and a counter electrode in contact with an electroconductive biocompatible fluid to form an electrochemical cell; and
    applying a time-varying potential, through the electrochemical cell, to the primary electrode,
    wherein the potential is characterized by a waveform having a maximum potential effectively anodic to meet or exceed the corrosion potential of the primary electrode, thereby corroding the primary electrode.

2. The method of claim 1, wherein the primary electrode is a metal electrode.

3. The method of claim 2, wherein the waveform has a minimum potential effectively cathodic to be below the value where re-deposition of metal ions on the metal electrode can substantially occur.

4. The method of claim 2, wherein the metal electrode comprises a metal selected from the group consisting of gold, platinum, silver, aluminum, chromium, copper, molybdenum, nickel, palladium, tantalum, titanium, tungsten, and zinc.

5. The method of claim 1, wherein the primary electrode has a thickness between about 100 and 1000 nm.

6. The method of claim 1, wherein the primary electrode comprises a reservoir cap of a microchip device for the release of molecules or exposure of device reservoir contents.

7. The method of claim 1, wherein the primary electrode comprises a polymer.

8. The method of claim 1, wherein the biocompatible fluid is a biological fluid.

9. The method of claim 8, wherein the biological fluid is selected from the group consisting of blood, plasma, lymph, extracellular matrix, interstitial fluid, serum, saliva, cerebrospinal fluid, gastrointestinal fluids, semen, and urine.

10. The method of claim 1, wherein the biocompatible fluid is selected from the group consisting of saline solutions, buffer solutions, pharmaceutical carrier solutions, and fermentation broths.

11. The method of claim 1, wherein the biocompatible fluid is in vitro.

12. The method of claim 1, wherein the biocompatible fluid is in vivo in a human or animal.

13. The method of claim 1, wherein the electrochemical cell consists of two electrodes.

14. The method of claim 1, wherein the electrochemical cell further comprises a reference electrode, which is placed in contact with the biocompatible fluid.

15. The method of claim 1, wherein the waveform is selected from the group consisting of square waves, sine waves, triangle waves, sawtooth waves, and combinations thereof.

16. A microchip device for the release or exposure of reservoir contents comprising:
    a substrate having reservoirs containing contents, wherein the reservoirs have reservoir caps which comprise a primary electrode; and
    controlled-potential instrumentation for applying a time-varying potential at a frequency between about 0.1 and 10,000 Hz to the primary electrode in an amount effective to corrode the primary electrode when placed in contact with an electroconductive fluid, said instrumentation comprising a counter electrode.

17. The microchip device of claim 16, wherein the time varying potential is characterized by a waveform having a maximum potential effectively anodic to meet or exceed the corrosion potential of the primary electrode.

18. The microchip device of claim 16, wherein the primary electrode is a metal electrode.

19. The microchip device of claim 18, wherein the waveform has a minimum potential effectively cathodic to be below the value where re-deposition of metal ions on the metal electrode can substantially occur.

20. The microchip device of claim 18, wherein the metal electrode comprises a metal selected from the group consisting of gold, platinum, silver, aluminum, chromium, copper, molybdenum, nickel, palladium, tantalum, titanium, tungsten, and zinc.

21. The microchip device of claim 16, wherein the primary electrode comprises a polymer.

22. The microchip device of claim 16, wherein the instrumentation for applying a time-varying potential further comprises a reference electrode.

23. The microchip device of claim 16, wherein the primary electrode has a thickness between about 100 and 1000 nm.

24. The microchip device of claim 16, wherein the reservoir contents comprise a drug, a biosensor, or a combination thereof.

25. A method of releasing or exposing the reservoir contents of a device at a site, the method comprising:
    providing at a site a device which comprises
    a substrate,
    at least two reservoirs in the substrate,
    reservoir contents in each of the at least two reservoirs,
    at least two reservoir caps, each reservoir cap covering one of the at least two reservoirs and comprising a primary electrode, and
    controlled-potential instrumentation, which comprises a counter electrode, for applying a time-varying potential at a frequency between about 0.1 and 10,000 Hz to the primary electrode;
    placing the primary electrode and the counter electrode in contact with an electroconductive fluid to form an electrochemical cell; and
    applying a time-varying potential, through the electrochemical cell, to the primary electrode to corrode the primary electrode in an amount effective to disintegrate the reservoir cap and release or expose the reservoir contents.

26. The method of claim 25, wherein the potential is characterized by a waveform having a maximum potential effectively anodic to meet or exceed the corrosion potential of the primary electrode.

27. The method of claim 25, wherein the primary electrode is a metal electrode.

28. The method of claim 27, wherein the waveform has a minimum potential effectively cathodic to be below the value where re-deposition of metal ions on the metal electrode can substantially occur.

29. The method of claim 25, wherein the electroconductive fluid is a biocompatible fluid.

30. The method of claim 29, wherein the electroconductive fluid is a biological fluid.

31. The method of claim 30, wherein the biological fluid is selected from the group consisting of blood, plasma, lymph, extracellular matrix, interstitial fluid, serum, saliva, cerebrospinal fluid, gastrointestinal fluids, semen, and urine.

32. The method of claim 25, wherein the biocompatible fluid is selected from the group consisting of saline solutions, buffer solutions, pharmaceutical carrier solutions, and fermentation broths.

33. The method of claim 25, wherein the electroconductive fluid is in vivo in a human or animal.

34. A method for enhancing corrosion of an electrode in a biocompatible fluid, the method comprising:

placing a primary electrode and a counter electrode in contact with an electroconductive biocompatible fluid to form an electrochemical cell; and applying a time-varying potential, at a frequency between about 0.1 and 10,000 Hz, through the electrochemical cell, to the primary electrode, wherein the potential is characterized by a waveform having a maximum potential effectively anodic to meet or exceed the corrosion potential of the primary electrode, thereby corroding the primary electrode.

35. The method of claim 34, wherein the time-varying potential is applied at a frequency between about 1 and 100 Hz.

36. The method of claim 34, wherein the time-varying potential is applied at a frequency between about 1 and 10 Hz.

37. A method of releasing or exposing the reservoir contents of a microchip device at a site, the method comprising:

providing at a site a microchip device which comprises (i) a substrate having reservoirs containing contents covered by reservoir caps which comprise a primary electrode, and (ii) means for applying a time-varying potential to the primary electrode in an amount effective to corrode the primary electrode when placed in contact with an electroconductive fluid, said means comprising a counter electrode;

placing the primary electrode and the counter electrode in contact with an electroconductive fluid to form an electrochemical cell; and applying a time-varying potential at a frequency between about 0.1 and 10,000 Hz, through the electrochemical cell, to the primary electrode to corrode the primary electrode in an amount effective to disintegrate the reservoir cap and release or expose the reservoir contents.

38. The method of claim 37, wherein the time-varying potential is applied at a frequency between about 1 and 100 Hz.

39. The method of claim 37, wherein the time-varying potential is applied at a frequency between about 1 and 10 Hz.

40. A device for the release or exposure of reservoir contents comprising:

a substrate;

at least two reservoirs in the substrate;

reservoir contents in each of the at least two reservoirs;

at least two reservoir caps, each reservoir cap covering one of the at least two reservoirs and comprising a primary electrode; and controlled-potential instrumentation for applying a time-varying potential to the primary electrode to corrode the primary electrode when placed in contact with an electroconductive fluid, wherein the controlled-potential instrumentation comprises a waveform generator and a potentiostat.

* * * * *